(12) United States Patent
Niedzwiecki et al.

(10) Patent No.: US 11,135,196 B1
(45) Date of Patent: Oct. 5, 2021

(54) PHARMACEUTICAL COMPOSITION AND ITS USE TO INHIBIT MEMBRANE ACE2 EXPRESSION

(71) Applicant: Matthias W Rath, Aptos, CA (US)

(72) Inventors: Aleksandra Niedzwiecki, Aptos, CA (US); Matthias W Rath, Aptos, CA (US); Vadim O Ivanov, Castro Valley, CA (US); Anna Goc, Sanjose, CA (US)

(73) Assignee: Matthias W. Rath, Henderson, NV (US)

( * ) Notice: Subject to any disclaimer, the term of this patent is extended or adjusted under 35 U.S.C. 154(b) by 0 days.

(21) Appl. No.: 17/196,121

(22) Filed: Mar. 9, 2021

Related U.S. Application Data

(60) Provisional application No. 63/008,560, filed on Apr. 10, 2020, provisional application No. 63/042,821, filed on Jun. 23, 2020.

(51) Int. Cl.

| | | |
|---|---|---|
| *A61K 31/375* | (2006.01) | |
| *A61K 31/353* | (2006.01) | |
| *A61K 31/201* | (2006.01) | |
| *A61K 31/30* | (2006.01) | |
| *A61P 31/14* | (2006.01) | |
| *A61K 36/484* | (2006.01) | |
| *A61K 33/30* | (2006.01) | |

(52) U.S. Cl.
CPC .......... *A61K 31/375* (2013.01); *A61K 31/201* (2013.01); *A61K 31/353* (2013.01); *A61K 33/30* (2013.01); *A61K 36/484* (2013.01); *A61P 31/14* (2018.01)

(58) Field of Classification Search
None
See application file for complete search history.

(56) References Cited

FOREIGN PATENT DOCUMENTS

| | | | |
|---|---|---|---|
| CN | 102028225 A | * | 4/2011 |
| CN | 108432668 A | * | 8/2018 |
| JP | 2010094084 A | * | 4/2010 |
| RU | 2462871 C2 | * | 10/2012 |

* cited by examiner

*Primary Examiner* — Alton N Pryor
(74) *Attorney, Agent, or Firm* — Geeta Kadambi; Riddhi IP LLC

(57) ABSTRACT

The study shows that ascorbic acid and its combination with some natural compounds could be included in developing preventive and therapeutic approaches toward the current pandemic. Some natural compounds were effective in lowering ACE2 cellular expression, with the highest inhibitory effects observed for baicalin (75%) and theaflavin (50%). Significantly, combinations of these and other test compounds with ascorbic acid further decreased ACE2 expression. The highest impact of ascorbate on ACE2 expression was noted when combined with theaflavin (decrease from 50% to 87%), zinc aspartate (decrease from 22% to 62%), and with 10-undecenoic acid (from 18% to 53%). Our study provides valuable experimental confirmation of the efficacy of micronutrients in controlling ACE2 expression—the coronavirus cellular "entry" point. It further validates the importance of nutrient interactions in various aspects of cellular metabolism and in considering potential therapeutic applications of nutrient-based approaches.

10 Claims, 13 Drawing Sheets
Specification includes a Sequence Listing.

PHARMACEUTICAL COMPOSITION AND ITS USE TO INHIBIT MEMBRANE ACE2 EXPRESSION

CROSS REFERENCE TO RELATED APPLICATIONS

This application claims priority to U.S. Provisional application 63/008,560 filed on 10 Apr. 2020 and U.S. Provisional application 63/042,821 filed on 23 Jun. 2020. These disclosures are hereby incorporated by this reference in their entirety for all of their teachings. This application contains sequence listing that has been submitted as an ASCII file named RIPLLC018033SEQ_ST25.txt, the date of creation 4/9/2021, and the size of the ASCII text file in bytes is 2 kb.

FIELD OF STUDY

This disclosure relates to inhibiting cell entry of viruses that uses angiotensin converting enzyme 2 (ACE2) receptors by using a pharmaceutical composition containing vitamin C and other natural compounds.

BACKGROUND

The current COVID-19 pandemic signifies one of the largest threats to global health in moderate history. Despite major effort, thus far, neither an effective vaccine nor safe drugs have become available as promising strategies for the global containment of this viral pandemic. Thus, there exists an urgent need for effective preventive and therapeutic strategies that are not confined to the more affluent parts of the world, but can offer global solutions.

Coronaviruses, including the subtype that causes the current pandemic, are known to enter body cells via a specific receptor, the Angiotensin-Converting-Enzyme 2 (ACE2), which is expressed by many cell types, including the lung epithelial cells and endothelial cells of the vascular system.

SUMMARY

The instant disclosure relates to inhibiting cell entry of viruses using ACE2 receptors by using a composition containing vitamin C and other natural compounds. In one embodiment, vitamin C is used to inhibit ACE2 receptor expression in epithelial cell and endothelial cell-which is considered the entry point for severe acute respiratory syndrome coronavirus 2 (SARS-CoV-2).

In one embodiment, a pharmaceutical composition comprising of one or more of the following compounds: L-ascorbic acid, magnesium ascorbate, calcium ascorbate, ascorbyl palmitate, ascorbyl phosphate, sodium ascorbyl phosphate or another form of ascorbate individually or in combination with other active natural and synthetic products. A pharmaceutical composition for the prevention and treatment of viral infections and/or viral diseases in humans and other species is disclosed.

A pharmaceutical composition consisting of ascorbic acid and natural compounds are disclosed. In another embodiment, natural compounds alone are used for treating infected patients by inhibiting angiotensin converting enzyme 2 expression for viral entry is disclosed. In another embodiment, the natural compounds are at least one of a baicalein, theaflavin, licorice, 10-Undeceonic acid that are used alone or in combination with ascorbic acid to treat SARS-CoV-2 patients.

The physiological every day dose for mammal for each component is: the ascorbic acid in the range of 10 mg to 200000 mg for mammal consumption baicalein, theaflavin at a range of up to 2,000 mg each, Zinc aspartate is in the range of 0.1 mg-200 mg (as elemental zinc), licorice in the range of 1 mg-200 mg/day, 10-undecenoic acid in the range of 1 mg-200 g.

A pharmaceutical composition for the prevention and treatment of viral infections that use cellular receptors for viral entry on the surface of epithelial cells, endothelial cells and/or other cell types is disclosed. A pharmaceutical composition for the prevention and treatment of viral infections/diseases that use angiotensin converting enzyme 2 (ACE2) receptors on the surface of epithelial cells, endothelial cells and other cell types for viral entry is disclosed.

A pharmaceutical composition for the prevention and treatment of infections with Severe acute respiratory syndrome-related coronaviruses (SARS-CoV-1) that uses angiotensin converting enzyme 2 (ACE2) receptors on the surface of epithelial cells, endothelial cells and other cell types for viral entry is disclosed.

A pharmaceutical composition for the prevention and treatment of infections with Middle East respiratory syndrome-related coronavirus (MERS-CoV) that uses angiotensin converting enzyme 2 (ACE2) receptors on the surface of epithelial cells, endothelial cells and other cell types for viral entry is disclosed.

A pharmaceutical composition for the prevention and treatment of infections with severe acute respiratory syndrome coronavirus 2 (SARS-CoV-2/COVID-19) that uses angiotensin converting enzyme 2 (ACE2) receptors on the surface of epithelial cells, endothelial cells and other cell types for viral entry is disclosed. A pharmaceutical composition for oral intake at physiological concentration is disclosed.

A pharmaceutical composition for intravenous application, for use as aerosol, inhalation solution, nasal or mouth spray, tooth paste, mouthwash, skin cream, skin patch, suppository or any other medically acceptable form of application is disclosed. A pharmaceutical composition were the compounds are applied in form of a physical mixture of the individual components is disclosed.

A pharmaceutical composition where two or more of the compounds are chemically bound/covalently linked to each other. A pharmaceutical composition comprising carriers, stabilizers and/or other medically acceptable additives is disclosed.

A pharmaceutical composition where one or more of the compounds are covalently linked to a carrier molecule. A pharmaceutical composition to be applied to the patient in form of nanoparticles or any other medically acceptable delivery form is disclosed.

BRIEF DESCRIPTION OF FIGURES

Example embodiments are illustrated by way of example and not limitation in the figures of the accompanying drawings, in which like references indicate similar elements and in which:

FIGS. 11A, 11B and 11C shows general mechanism of viral infection (prior art).

Figure 1:
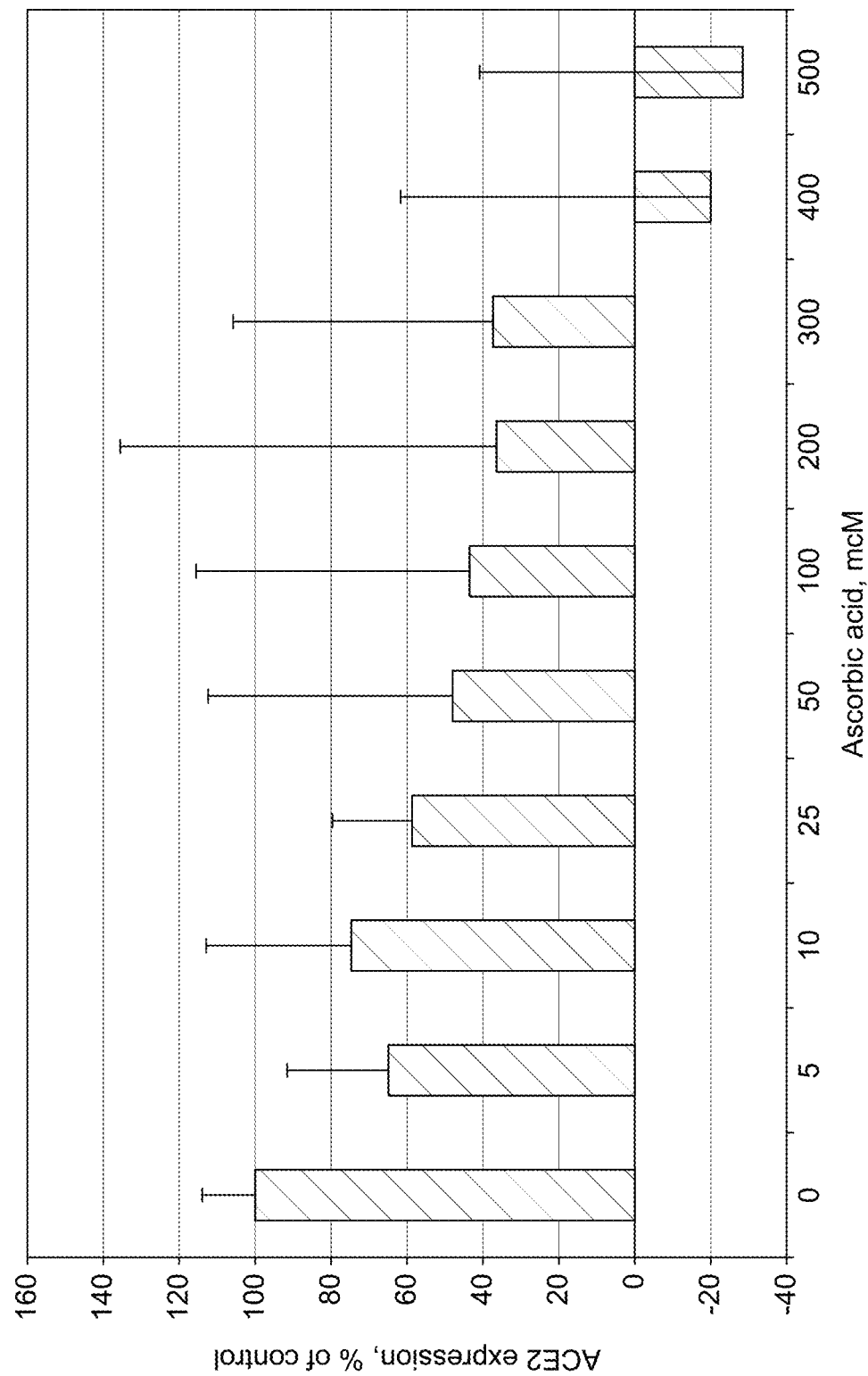
FIG. 1 shows Effects of Ascorbic Acid (7 days supplementation) on ACE2 expression in AoEC.

Others features of the present embodiments will be apparent from the accompanying drawings and from the detailed description that follows.

DETAILED DESCRIPTION

ACE2 is an integral membrane protein present on many cells throughout the human body with its strong expression in the cardiovascular, gastrointestinal, renal and pulmonary system. Among the cell types expressing ACE2, vascular endothelial cells and alveolar cells of the lungs were particularly well studied. ACE2-expressing cells may act as target cells and their distribution in the human body may indicate the potential infection routes of 2019-nCoV (Hamming 2004, Wan 2020).

Over the years we have successfully tested specific micronutrients as natural inhibitors of viral infections and identified common targets for these natural compounds—independent of specific viral types. The results showed that vitamin C, especially in combination with other natural compounds such as lysine, green tea extract, selenium and other micronutrients, could affect key mechanisms associated with infection of human influenza virus H1N1 (Jariwalla 2007), bird flu H5N1 (Deryabin 2008), avian flu H9N2 in vitro and in vivo (Barbour 2009) as well as HIV (Jariwalla 2010).

These micronutrients were effective in inhibiting viral infectivity, multiplication, spread and protected infected tissues from infection-related damage. Moreover, these natural components have shown to have better and protracted efficacy in protecting infected cells against damage when compared to antiviral drugs, such as Tamiflu and Amantadine (Deryabin 2008).

In an effort to provide practical solutions for the control of the current pandemic we decided to look for a potential role of vitamin C on the expression of ACE2 receptors. We assumed that this vitamin could potentially inhibit the expression of these cellular "anchors" required for viral attachment and entry. In that assumption, we were encouraged by reports from clinics in China earlier this year that successfully used high-dose intravenous vitamin C to combat COVID-19 in patients.

Methods and Materials

Our studies established that vitamin C can decreases the expression of ACE2 in vascular endothelial cells—the decisive receptor for the cellular binding and entry of the corona virus that causes the current pandemic. A substantial decrease can already be observed at relatively low concentrations of the vitamin, obtainable by oral intake in form of dietary supplementation.

Expression of Angiotensin Converting Enzyme 2 (ACE-2) in Human Aortic Endothelial Cells (HAEC): Cultured Cells: Human Aortic Endothelial Cells (HAEC) purchased from Lonza were cultured in EGM-2 growth medium (Lonza) in plastic flasks at 37° C. and 5% CO2. For experiment cells were plated to collagen-covered 96 well plastic plate (Corning) in 100 mcl EGM-2 medium and were grown to confluent layer for 7 days.

Cell supplementation with ascorbic acid: Cells were supplemented with indicated doses of ascorbic acid (Sigma) in EGM-2 for 7 days with six repetitions for each dose. Experimental medium was changed every 2-3 days with freshly prepared ascorbic acid solution in EGM-2.

ACE-2 ELISA assay: Plate wells were washed two times with phosphate buffered saline (PBS) and fixed with 3% formaldehyde/0.5% Triton X100/PBS solution for 1 h at 4° C., then washed four times with PBS. 200 mcl of 1% bovine serum albumin BSA, Sigma) in PBS were added and plate was incubated at 4° C. overnight. Mouse monoclonal anti ACE-2 antibody (Santa Cruz Biotechnology) was added in 100 mcl 1% BSA/PBS for 1.5 h incubation at room temperature (RT). After three wash cycles with 0.1% BSA/PBS wells were supplied with 100 mcl anti mouse IgG antibodies conjugated with horse radish peroxidase (HRP, Rockland) for 1 h at RT. After three wash cycles with 0.1% BSA/PBS retained HRP activity was determined by incubation 100 mcl TMB substrate solution (Sigma) for 20 min at RT and addition of 50 mcl of 1N H2SO4 by measuring optical density at 450 nm with micro plate reader (Molecular Devices). Results are expressed as percentage of ascorbate-free Control (mean+/−SD, n=6).

TABLE 1

| Reagents |
| --- |
| Cell Culture |
| 3/9 AoEC 2x 96 well plates seeded at 7 p |
| 3/16 Supplementations started in EGM-2 |
| Last additions - 03/20 |
| 03/23 cells wash 2x PBS |
| Incubate with 100 mcl/ell 3% |
| formaldehyde/PBS/0.5% Triton-X100 for 1h at 4° C. |
| Wash 4 PBS, add 200 mcl/well 1% BSA/PBS overnight at 4° C. |
| 03/24 Incubate with 100 mcl/well anti ACE2 |
| (1/5 k Santa Cruz Biotech) for 1.5 h at |
| RT on shaker |
| Followed by 1/1 k anti MS PRX 1/25 h at RT |
| TMB substrate (Sigma) |

FIG. 1 shows studies in human endothelial cells showed that vitamin C is able to inhibit the expression of the ACE2 receptor, the cellular entry site for the virus causing COVID-19, in a dose dependent manner. Even at low concentrations of 50-100 mcM—achievable trough dietary supplementation with vitamin C—the vitamin was able to suppress the expression of the ACE 2 receptor by over 50%. Higher concentration of vitamin C that are achievable by intravenous injections lead to a further inhibition in ACE2 expression by these human cells.

FIGS. 2A, 2B, 2C, 2D, 2E, 2F and 2G shows effects of ascorbic acid on ACE2 receptor expression at the protein level. Western blot analysis of ACE2 protein expression in human small alveolar epithelial cells and human lung microvascular cells incubated in the presence of various concentrations of ascorbic acid. Quantitative analysis of the effects of ascorbic acid (AsA) on ACE2 is done as follows.

Materials and methods: Reagents—All reagents were purchased from Sigma-Aldrich (St. Louis, Mo., USA) if not indicated otherwise. Quercetin dihydrate and zinc aspartate were from Powder City (York, Pa., USA). *Ginkgo biloba* extract was from Monterey Bay Spice Company (Monterrey, Calif., USA), and Theaflavins from Cayman Chemicals (Ann Arbor, Mich., USA).

Cultured Cells

Human Small Airways Epithelial Cells (SAEC), purchased from ATCC, (Manassas, Va., USA) were cultured in Airways Epithelial Cells growth medium (ATCC) in plastic flasks at 37° C. and 5% CO2. For the experiments, the cells (passage 5-7) were plated to collagen-covered 96-well plates in 100 μL/well growth medium and were grown to confluent layer for 4 to 7 days. Human Microvascular Endothelial Cells isolated from lung (HMEC), purchased from Lonza, (Hayward, Calif., USA) were cultured in EGM-2 MV growth medium (Lonza) in plastic flasks at 37° C. and 5% CO2. For the experiments, cells at 5 to 7 passages were plated to collagen-covered 96-well plates in 100 μL/well EGM-2 MV medium and were grown for 3 to 5 days to reach confluent layer.

ACE2 ELISA Assay

For the experiments, cells were supplemented with indicated doses of tested compounds in 100 μL/well of cell growth medium for 6 days with fresh media supplementations every 2 to 3 days. Control cell growth media did not contain ascorbic acid. Culture plate wells were washed twice with phosphate buffered saline (PBS) and fixed with 3% formaldehyde/0.5% Triton X-100/PBS solution for 1 hour at 4° C., then washed 4 times with PBS. Two-hundred microliter of 1% bovine serum albumin-BSA (Sigma-Aldrich, St. Louis, Mo., USA) in PBS was added and the plate was incubated at 4° C. overnight. Rabbit polyclonal anti-ACE-2 antibodies (Sigma Aldrich, St. Louis, Mo., USA) were added in 100 μL/well 1% BSA/PBS solution for 1.5 hours incubation at room temperature (RT). After 3 wash cycles with 0.1% BSA/PBS wells were supplied with 100 μL/well of anti-rabbit IgG antibodies conjugated with horse radish peroxidase (HRP, Sigma, St. Louis, Mo., USA) for 1 hour at RT. After 3 wash cycles with 0.1% BSA/PBS the HRP activity retained was determined by incubation with 100 μL/well TMB substrate solution (Sigma-Aldrich, St. Louis, Mo., USA) for 20 minutes. at RT, followed by the addition of 50 μL/well of 1N H2SO4 and optical density measurement at 450 nm with microplate reader (Molecular Devices, San Jose, Calif., USA).

Figure 2A:
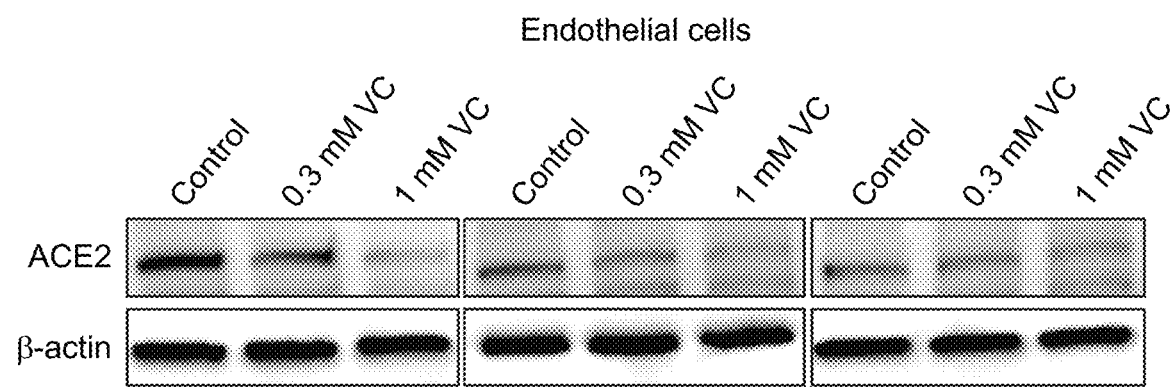
FIGS. 2A, 2B, 2C, 2D, 2E, 2F and 2G shows effect of different concentration of ascorbic acid onACE2 receptor expression at the protein level as shown by Western blots.
Figure 2B:
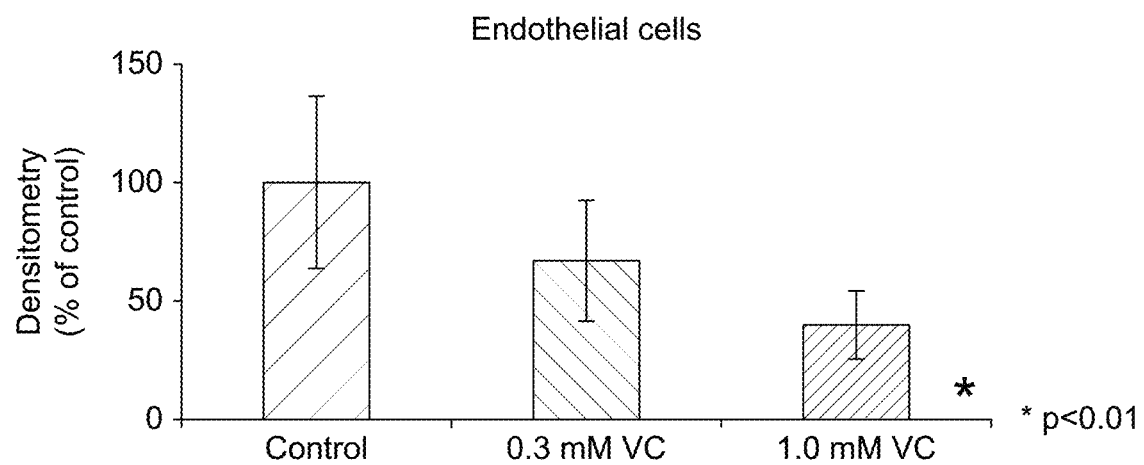

FIGS. 2A and 2B shows effects of different concentrations of ascorbate on ACE2 protein expression in SAEC and Human Microvascular Endothelial Cells (HMVEC) by Western blot. FIG. 2A shows that ascorbate used at 1 mM concentration can significantly lower ACE2 protein expression in human microvascular endothelial cells and human small airway epithelial cells as identified by Western blot in FIGS. 2F and 2G.

Results are expressed as a percentage of experimental addition—free control (mean±SD, n=6). Non-specific control (wells incubated without anti-ACE2 antibodies) mean value (n=6) was subtracted from all sample values.

Western blot: SAEC and HMEC were plated on 6-well plates and supplemented with 0.3, 0.6, 0.8, and 1 mM ascorbic acid, respectively. After 6 days whole SAEC and HMEC lysates, respectively, were prepared using lysis buffer (50 mM Tris-HCl [pH=7.4], 1% TritonX-100, 150 mM NaCl, 1 mM EDTA, 2 mM Na3VO4, and 1× Complete protease inhibitors [Roche Applied Science, Indianapolis, Ind., USA]). The protein concentration was measured by the Dc protein assay (Bio-Rad, Hercules, Calif., USA). Fifty microgram per well of protein was separated on 8% to 16% gradient SDS-PAGE gels (ie, Tris-based electrophoresis using standard Laemmle's method without (3-ME addition to sample buffer) and transferred to a PVDF membrane. Proteins were detected with commercially available anti-ACE-2 monoclonal antibody diluted 1:250 (R&D, Minneapolis, Minn., USA) and anti-β-actin antibody as a loading control (Cell Signaling, Danvers, Mass., USA).

qRT-PCR: SAEC and HMEC were plated on 6-well plates and stimulated with 0, 0.3, 0.6, 0.8, and 1.0 mM of ascorbic acid, respectively. After 6 days, total RNA was isolated using RNeasy Plus Mini Kit (Qiagen, Germantown, Md., USA). Next, 2500 ng of each isolate was transcribed in cDNA using $RT^2$ HT First Strand Kit (Qiagen, Germantown, Md., USA) and subjected to qRTPCR using specific primers for ACE2 (forward primer, SEQ ID. NO. 1-5'-TGGGCAAACTCTATGCTG-3'; and reverse primer, SEQ ID. NO. 2-5'-TTCATTGGCTCCGTTTCTTA-3) and β-actin (forward primer, SEQ ID. NO. 3-5'-CATCCGTAAA-GACCTCTATGCCAAC-3'; and reverse primer, SEQ ID. NO. 4-5'-ATGGAGCCACCGATCCACA-3'). The PCR was performed with a QuantiTect SYBR® Green PCR Kit as the source of 2.5 mM Mg2+, deoxynucleotides and HotStarTaq DNA polymerase, in addition to each primer used at a concentration of 0.3 μM in a 50 μL qPCR mixture (Qiagen, Germantown, Md., USA) in a BioRad CFX instrument (BioRad, Hercules, Calif., USA). The qPCR cycler conditions were programmed according to the manufacturer's recommendations and were as follows: an activation step at 95° C. for 15 minutes, 40 cycles of: denaturation at 94° C. for 15 seconds, annealing at 60° C. for 30 seconds, and extension at 72° C. for 30 seconds. To verify the specificity and identity of the qPCR product, melting curve analyses were performed. The amount of β-actin cDNA was used to normalize the sample amounts used for determinations. All samples were tested in duplicate PCR reactions and the mean of the reactions was used for calculating the expression levels.

Figure 2C:
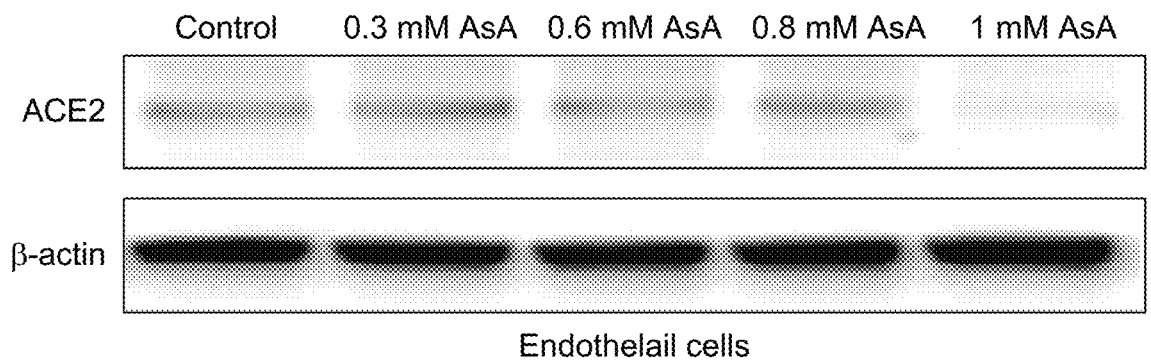
Figure 2D:
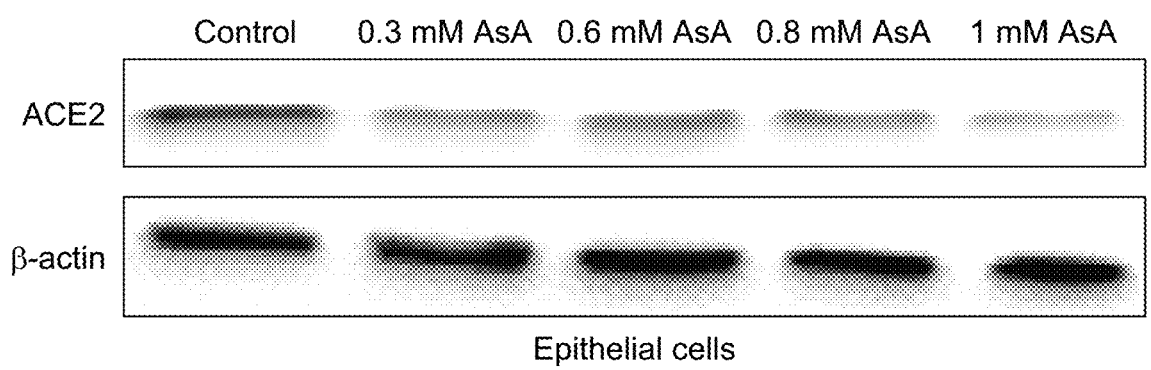
Figure 2E:
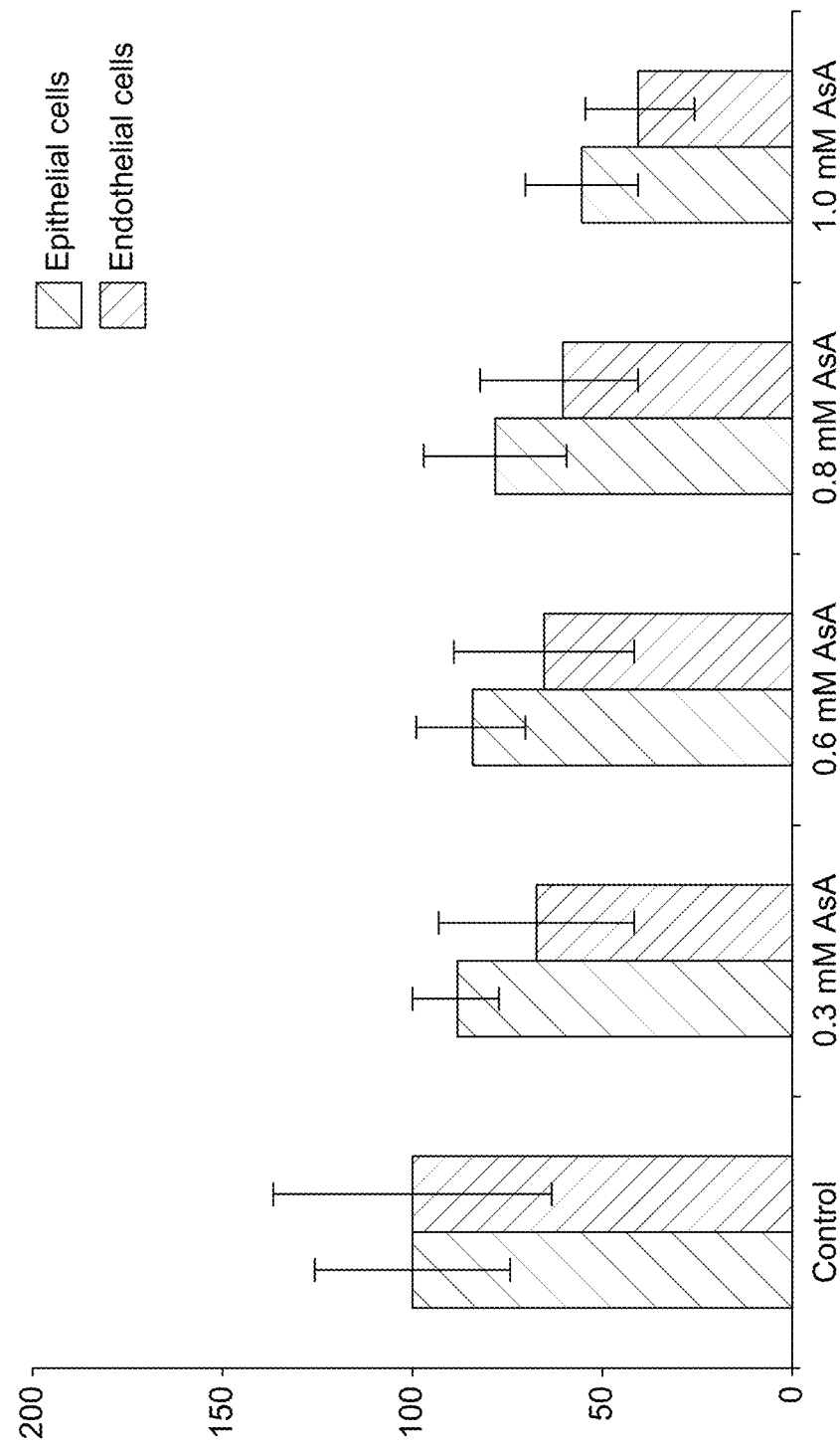
Figure 2F:
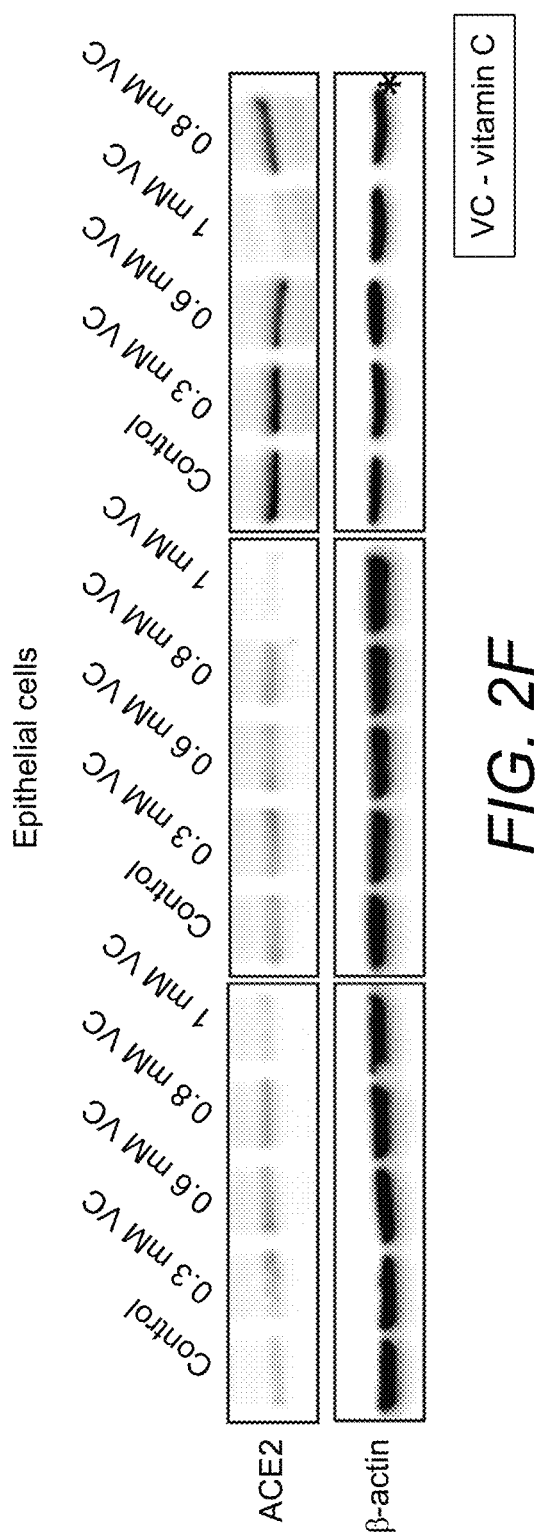
Figure 2G:
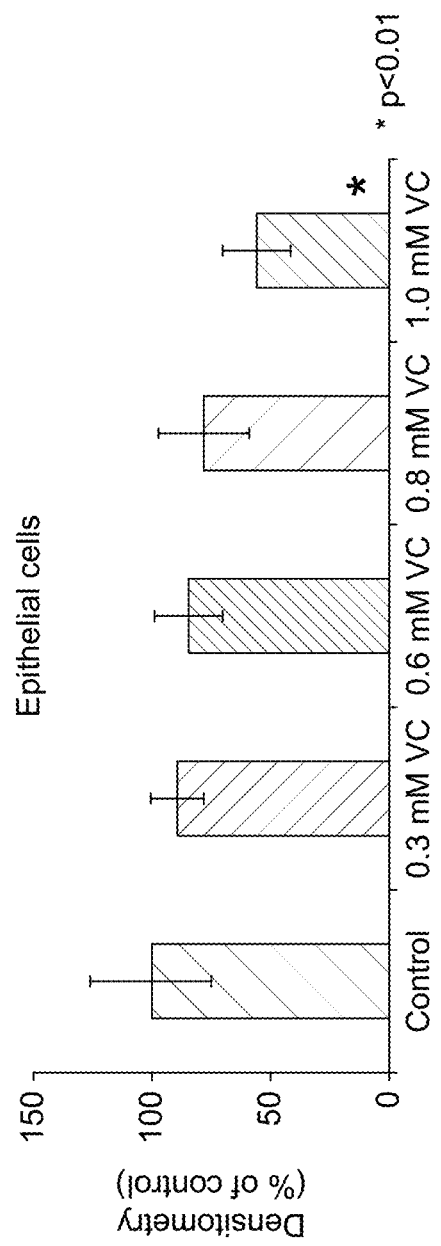

Results: Effects of ascorbic acid on ACE2 receptor expression at the protein level are shown respectively. The FIG. 2C shows the results of Western blot analysis of ACE2 protein expression in human small alveolar epithelial cells and human lung micro-vascular cells incubated in the presence of various concentrations of ascorbic acid for 6 days. Quantitative analysis (FIG. 2D) further confirms dose dependent trend in the reduction of ACE2 protein, starting from 0.3 mM ascorbic acid up to 1 mM. Statistically significant reduction of this protein by 55% and 60% was observed at 1.0 mM ascorbic acid in SAEC and HMEC cell lines, respectively.

This conclusion is further supported by the fact that the inhibiting effect of vitamin C on the expression of ACE2 receptors on endothelial cells is already achieved by relatively low concentrations of this vitamin that could be achieved by an optimum oral intake of this vitamin, e.g. by dietary supplements, High vitamin C concentrations achievable by its intravenous injections could explain the underlying mechanism of beneficial effects of high vitamin C doses in SARS-Co-V2 infected patients as reported in clinical trials (REF). One of the mechanisms would be a decrease in ACE2 receptors. The decrease of ACE2 expression at low and high concentrations of vitamin C suggests that the expression of this receptor is tightly regulated by this vitamin.

Figure 3:
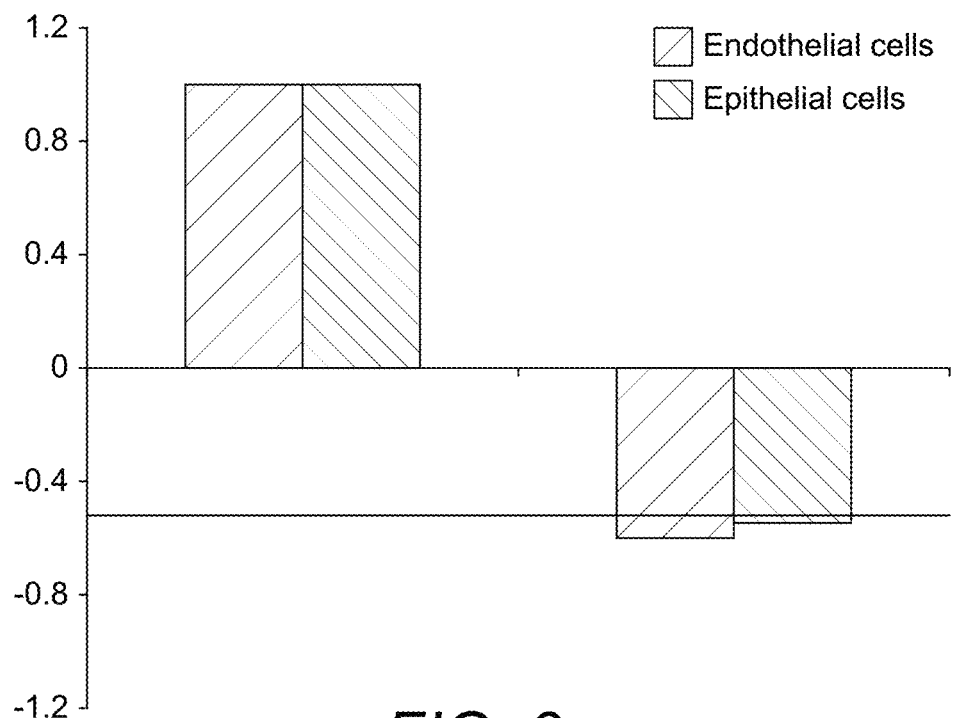
FIG. 3 shows effects of ascorbic acid on mRNA expression of ACE2 receptor protein. ACE2 expression at mRNA level in SAEC and HAEC in the presence of 1 mM ascorbic acid (AsA).

FIG. 3 shows effects of ascorbic acid on mRNA expression of ACE2 receptor protein in SAEC and HMEC in the presence of 1 mM ascorbic acid (AsA). The horizontal line marks change by 0.5-fold. Experiments were also done to see the effects of ascorbic acid on mRNA expression of ACE2 receptor protein. In order to assess further whether ascorbic acid can inhibit ACE2 expression at the RNA level we performed qRT-PCR analysis. The results in FIG. 3 show that in the presence of 1.0 mM ascorbic acid the ACE2 gene expression in SAEC and HMEC decreased by 0.61- and 0.54-fold, respectively. The down-regulating trend by ascorbic acid was evident in both types of cells, although it did not cross a standard cut-off value (ie, 0.5-fold of change).

Figure 4:
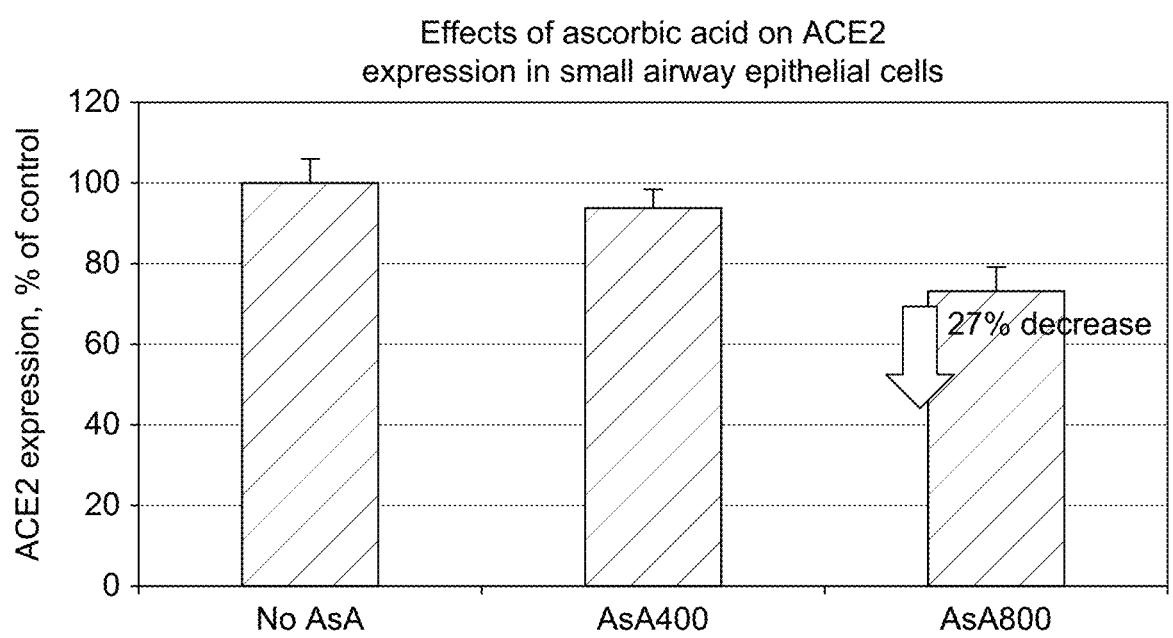
FIG. 4 shows effects of ascorbic acid on ACE2 expression in SAEC.

FIG. 4 shows effects of ascorbic acid on ACE2 expression in SAEC. FIG. 4 shows that at 800 mcM ascorbate concentration the membrane expression of ACE2 in these cells can be decreased by 27%.

Figure 5A:
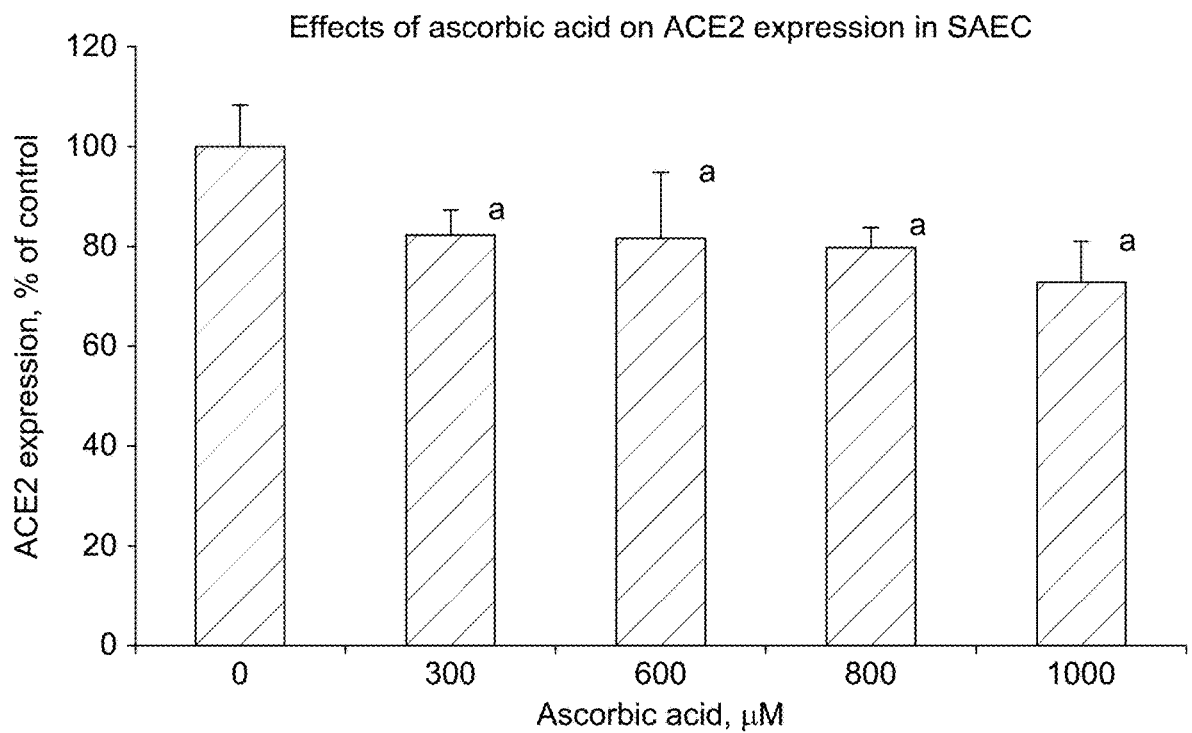
FIG. 5A and FIG. 5B shows changes in cellular expression of ACE2 on SAEC in presence of ascorbic acid and ascorbyl palmitate.
Figure 5B:
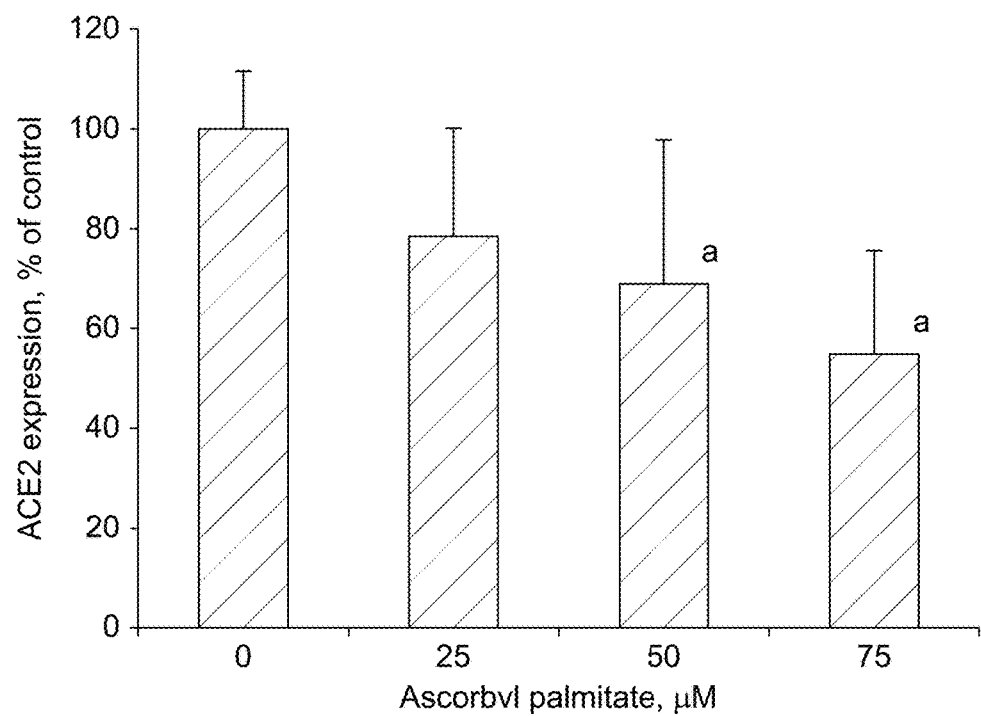

FIG. 5A Changes in cellular expression of ACE2 on SAEC in presence of ascorbic acid and ascorbyl palmitate. Changes in ACE-2 cellular expression on SAEC measured by a specific antibody affinity directed toward this receptor in the presence of various concentrations of ascorbic acid and its lipid-soluble derivative, ascorbyl palmitate (FIG. 5B). Effects of ascorbic acid on cellular expression of ACE2 receptors in the presence of natural compounds were studied. Although earlier studies using molecular modeling technology suggested several natural compounds as potential candidates against coronavirus, the experimental proof of their efficacy, in particular their direct effects on cellular ACE2 receptor targeted by SARS-CoV-2, were not evaluated. Understanding these aspects is critical since many of these natural compounds are available in our diet or can be taken as dietary supplements for different health aspects, including as preventive measures against viral infections. In the presence of ascorbic acid there was dose dependent decrease of ACE2 expression with about 18% decrease at 0.6 mM and 27% at 1.0 mM concentration (FIG. 5A). As presented on FIG. 5B, exposure of these epithelial cells to ascorbyl palmitate resulted in 50% inhibition of ACE2 expression, already at much lower concentrations compared to ascorbic acid of 75 µM. At higher concentrations (>100 µM) ascorbyl palmitate showed cytotoxic effects.

We conducted this study with human endothelial cells because they are known to express ACE2, but also because this cell type plays a particular role in the initiation and promotion of infectious diseases in general. Vitamin C deficiency facilitates the infectivity of viruses in general, e.g. by destabilizing the vascular connective tissue, causing gaps between endothelial cells and by weakening the vascular basement membrane (Gore 1965, Friederici 1966, Mahmoodian 1999). All these extracellular effects compromise the natural hairier function of the blood vessel wall, including the endothelial lining of lung capillaries.

While these data were obtained in vitro with human endothelial cells, they provide an important scientific explanation for the in vivo observations made with hospitalized COVID-19 patients, who recovered with intravenous application of vitamin C.

Figure 6:
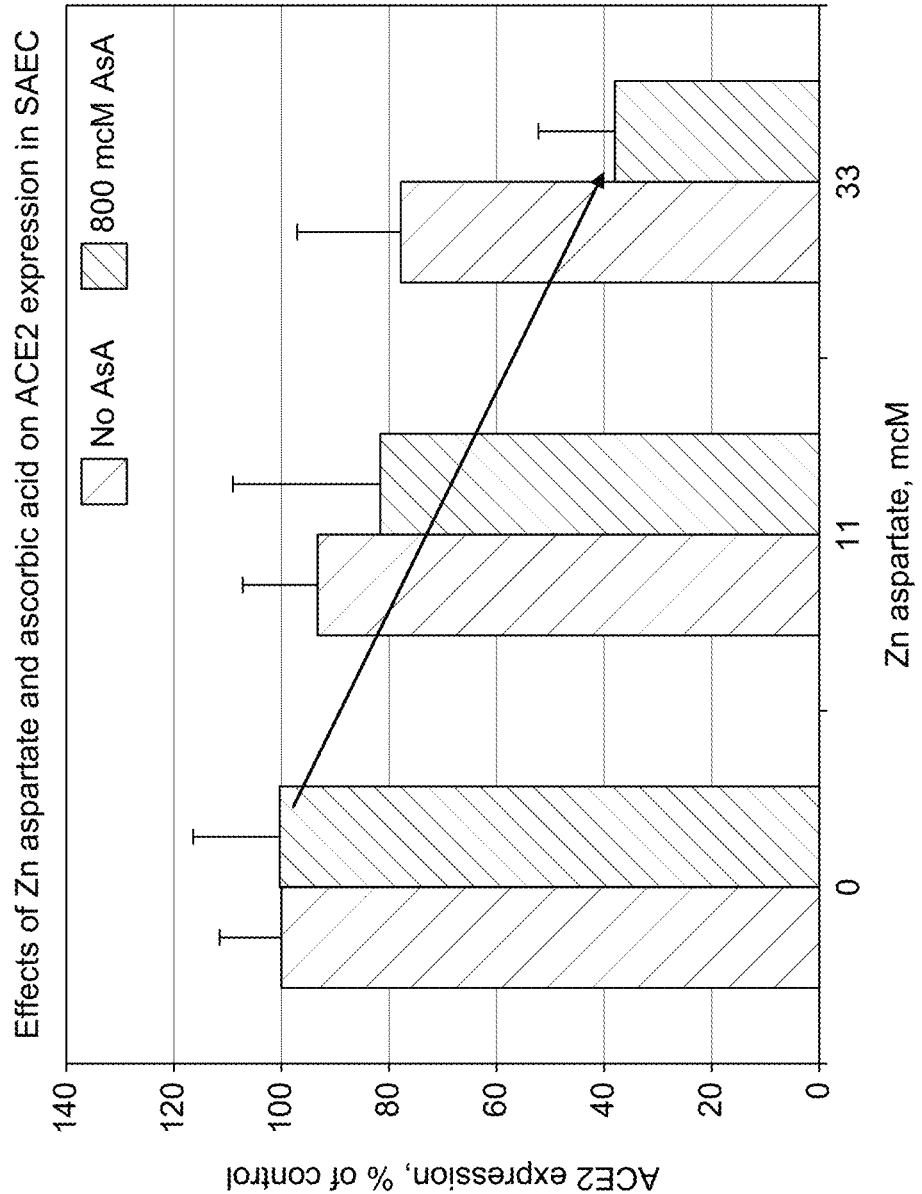
FIG. 6 shows effects of Zn aspartate and Ascorbic Acid on ACE2 expression in SAEC.
Figure 7:
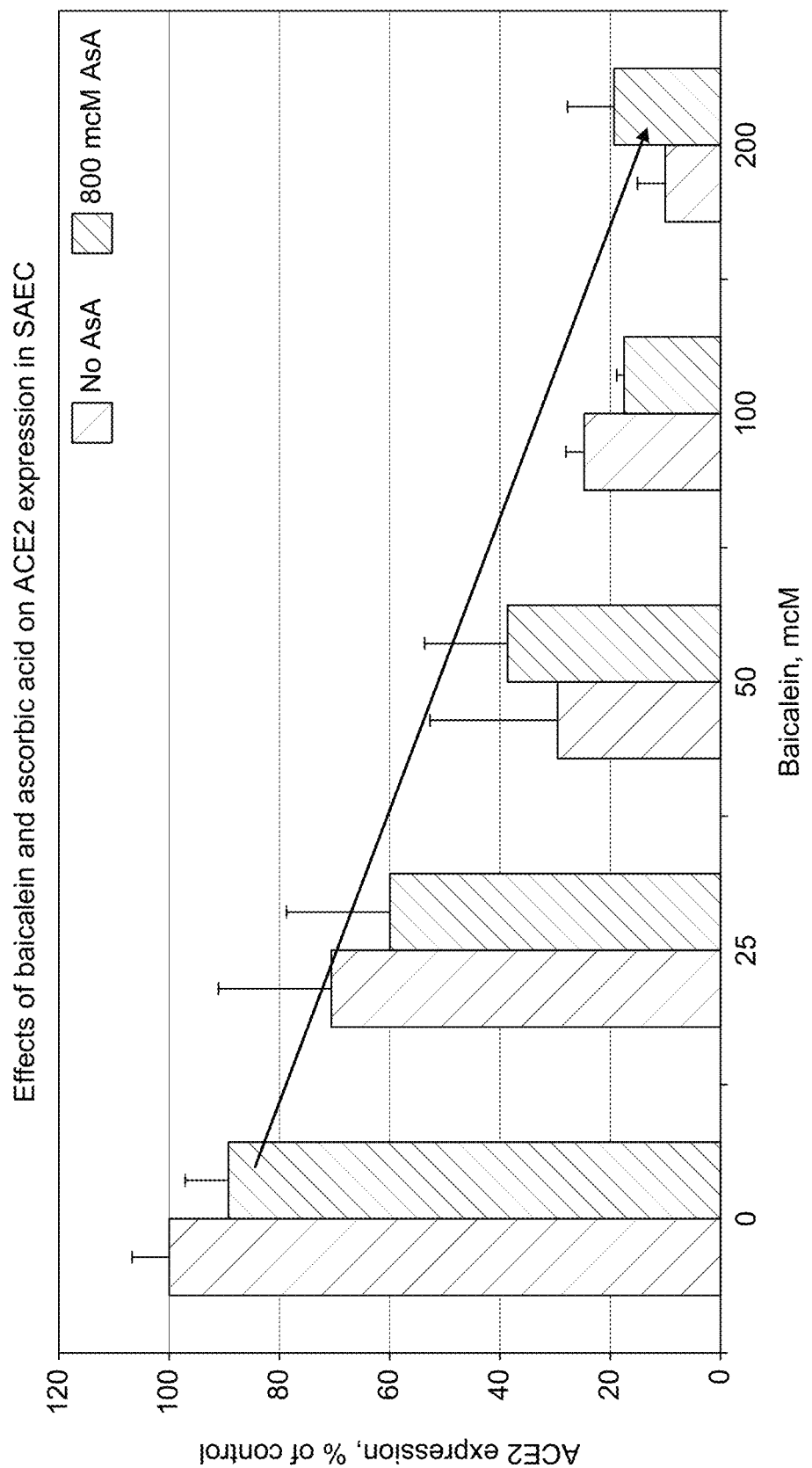
FIG. 7 shows effects of Baicalein and Ascorbic Acid on ACE2 expression in SAEC.
Figure 9:
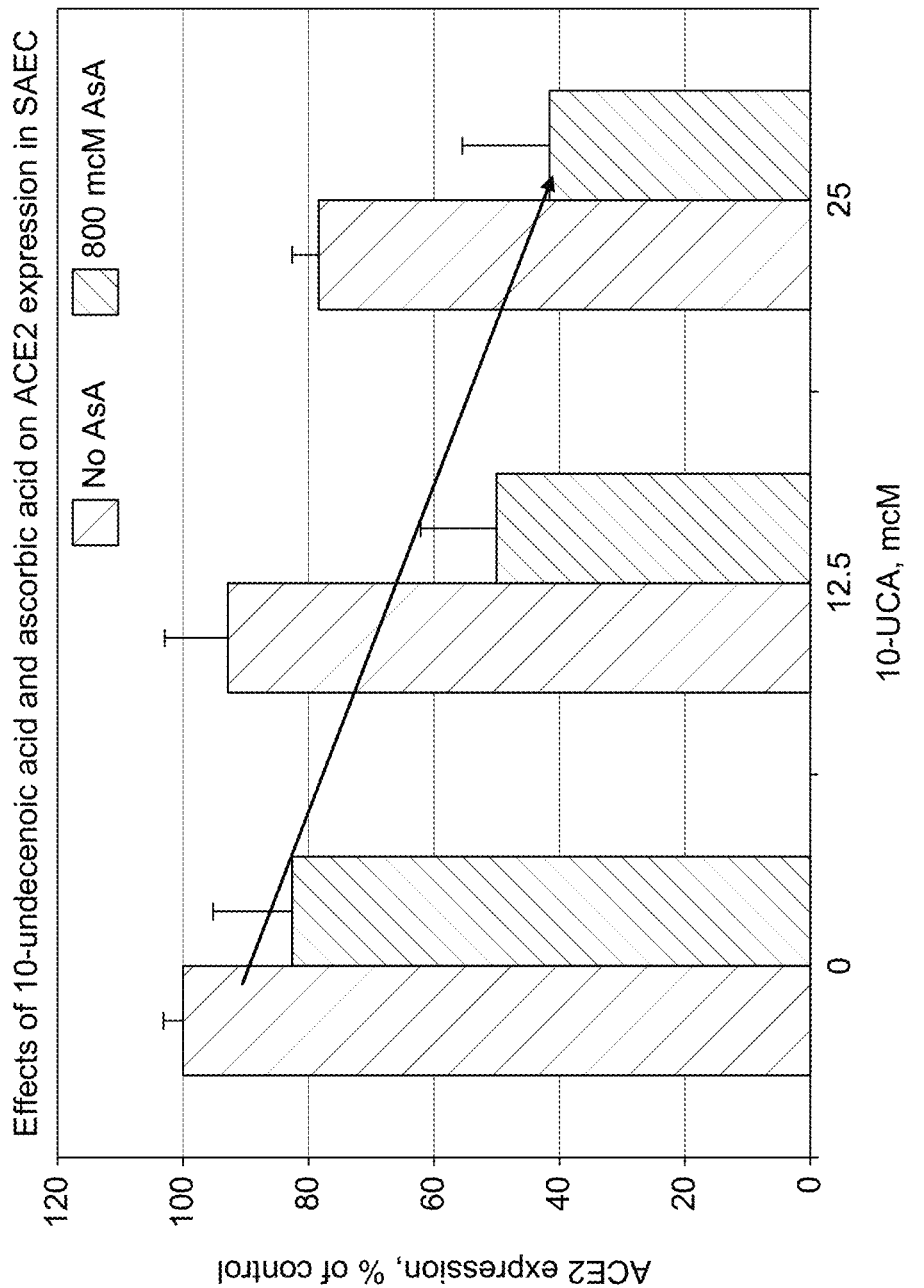
FIG. 9 shows effects of 10-Undecenoic Acid and Ascorbic Acid on ACE2 expression in SAEC.
Figure 10:
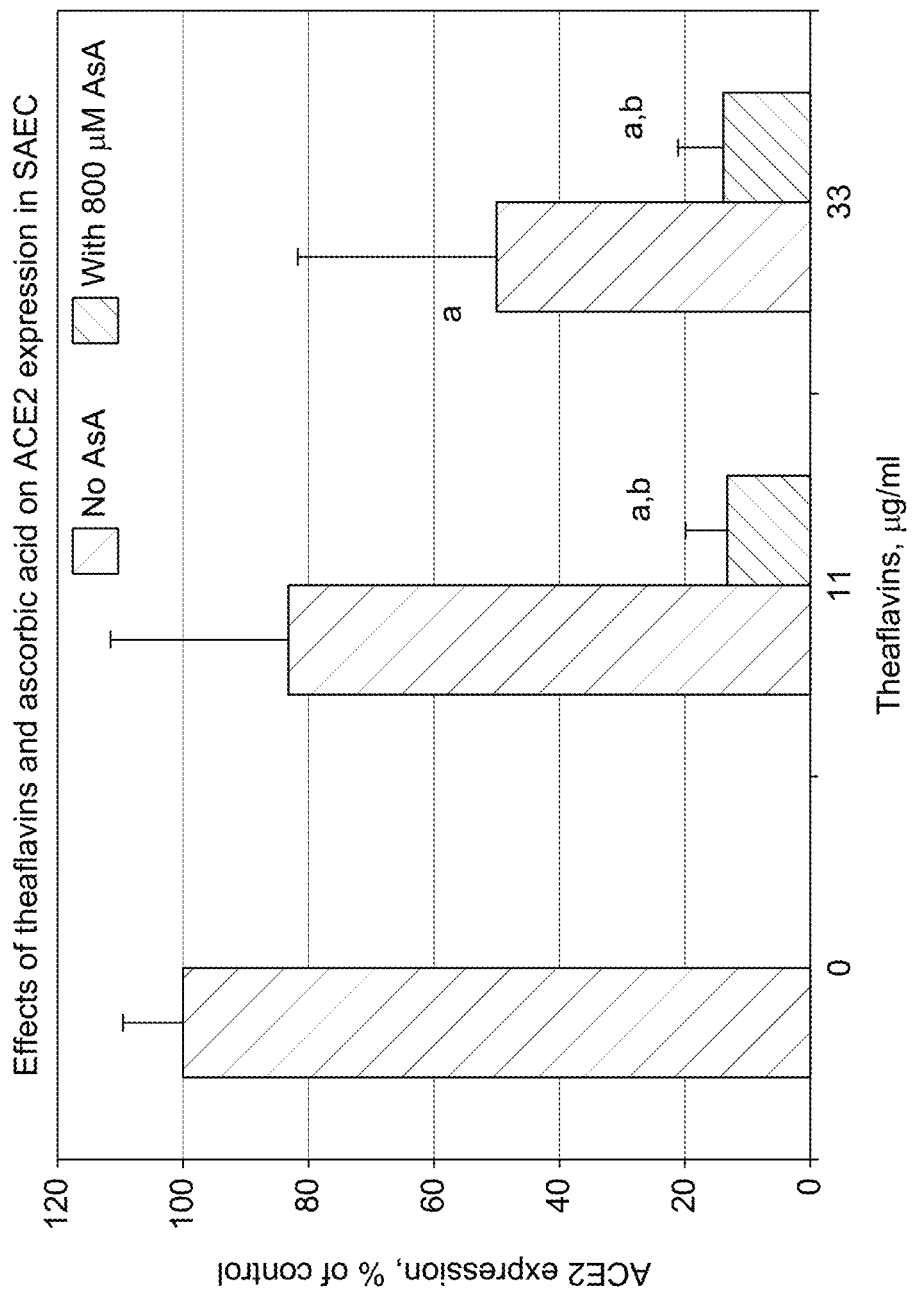
FIG. 10 shows effects of Theaflavin and Ascorbic Acid on ACE2 expression in SAEC.

In one embodiment, we evaluated changes in ACE2 expression in SAEC in the presence of select natural components applied individually and in combination with ascorbic acid. The results show that all these natural compounds had inhibitory effects on ACE2 expression in SAEC, but to different degrees. Theaflavin used individually inhibited ACE2 expression by about 50% at concentrations of 33 µg/mL and 50 µM respectively (FIG. 10). Combinations of these compounds with ascorbic acid further enhanced their inhibitory effects on ACE2 expression from 50% to 87%, in case of theaflavin and from 75% to 82% with baicalein. FIG. 6 shows that a combination of ascorbate with zinc aspartate increased zinc's inhibitory effect by an additional 40%, resulting in ACE2 expression inhibition by 62% by 2 compounds together Ascorbate combination with 10-undecanoic acid also decreased ACE2 expression from 18% (individual effect) to 53%, when combined with AA resulting in an additional 35% inhibitory effect (FIG. 9). Of all test ingredients, baicalein was the most effective and at 25 µM concentration was able to inhibit ACE2 expression by 75% compared to no ascorbate control (FIG. 7).

Subsequently, we evaluated changes in ACE2 expression in SAEC in the presence of select natural components applied individually and in combination with ascorbic acid. The results are presented in FIG. 7, FIG. 8, FIG. 9 and FIG. 10.

Figure 8:
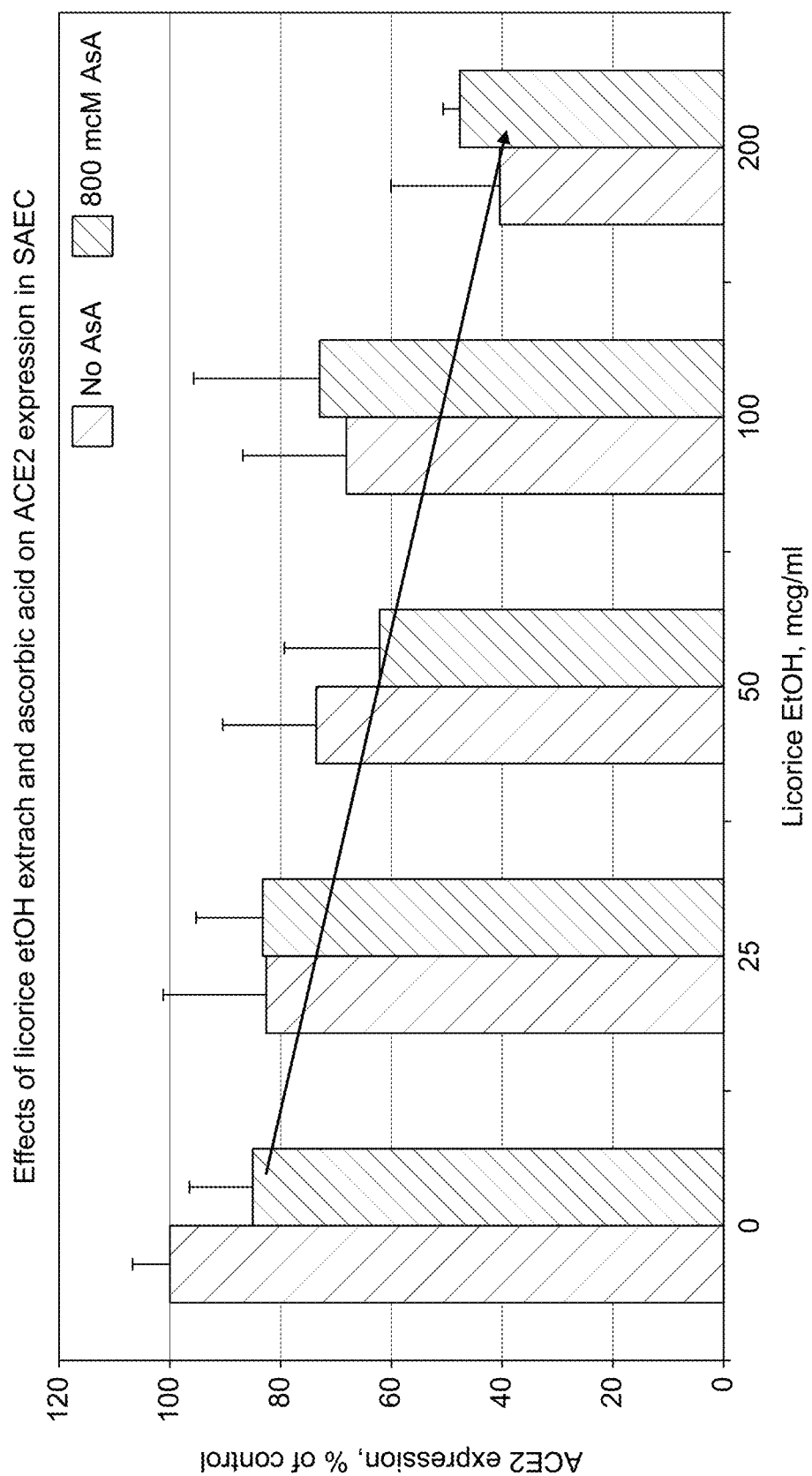
FIG. 8 shows effects of Licorice ethanol extract and Ascorbic Acid on ACE2 expression in SAEC.

The results show that all these natural compounds had inhibitory effects on ACE2 expression in SAEC, but to different degrees. Of all test ingredients, baicalein was the most effective and at 25 µM concentration was able to inhibit ACE2 expression by 75% compared to no ascorbate control (FIG. 7). FIG. 8 shows effects of Licorice ethanol extract and Ascorbic Acid on ACE2 expression in SAEC. Licorice by itself shows a significant drop in expression and in combination with ascorbic acid it has significant beneficial effect.

Theaflavin used individually inhibited ACE2 expression by about 50% at concentrations of 33 µg/ml and 50 µM respectively (FIG. 10). Combinations of these compounds with ascorbic acid further enhanced their inhibitory effects on ACE2 expression from 50% to 87%, in case of theaflavin and from 75% to 82% with baicalein. FIG. 6 shows that a combination of ascorbate with zinc aspartate increased zinc's inhibitory effect by an additional 40%, resulting in ACE2 expression inhibition by 62% by two compounds together Ascorbate combination with 10-undecanoic acid also decreased ACE2 expression from 18% (individual effect) to 53%, when combined with AA resulting in an additional 35% inhibitory effect (FIG. 9). NAC had the smallest effects on ACE2 expression in SAEC compared to other compounds (18% inhibition at 2 mM). However, NAC's combination with ascorbic acid further lowered ACE2 expression resulting in 26% inhibition (FIG. 4D).

Figures 11A, 11B, 11C:
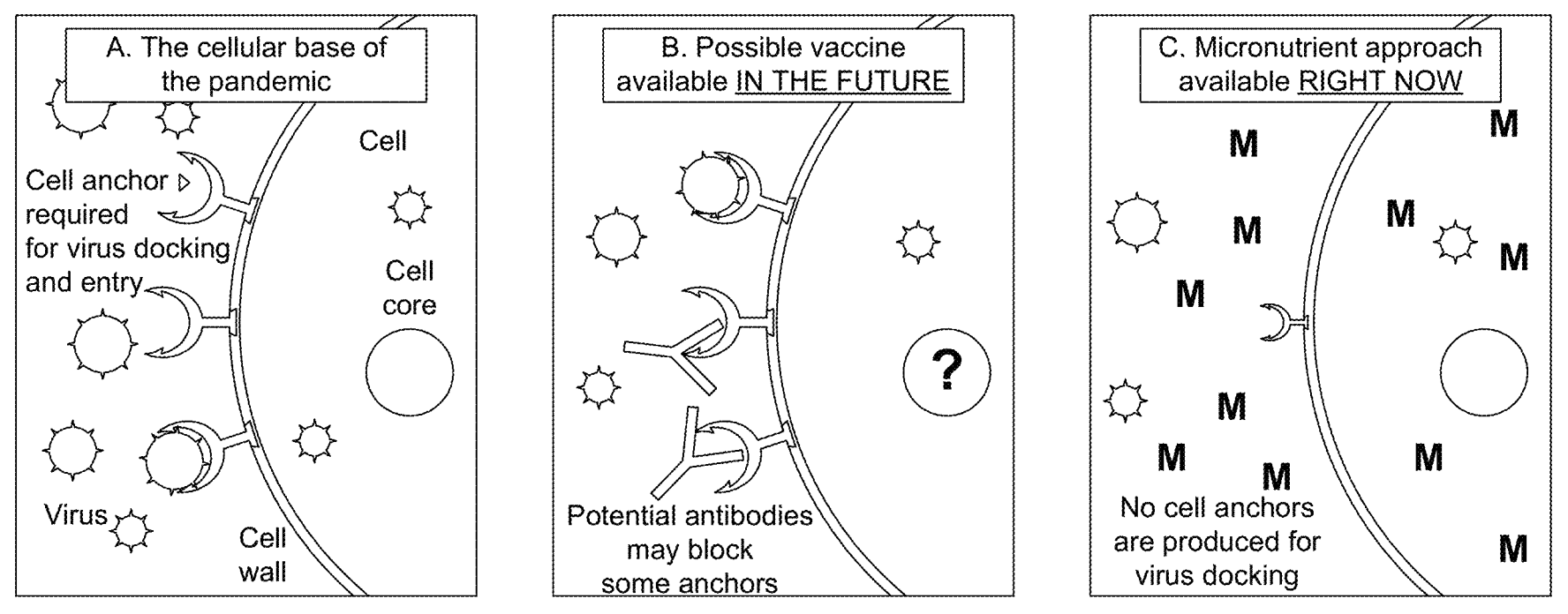

Based on these results we propose the anticipated mechanism of micronutrient effects on ACE2 expression (Figure. 11). FIG. 12 in three sections shows the general concept of virus activity FIG. 11A: The virus causing the current pandemic enters the vascular endothelial and lung epithelial cells via an 'anchor' (receptor) expressed in the cell wall. Without this anchor the virus cannot enter, FIG. 11B: Trying to block the entry of the virus into the cell by blocking this 'anchor', has become a prime target of vaccine development—with as yet unknown success. FIG. 11C: We have now shown in human endothelial cells that a composition of specific micronutrients is able to abolish the activity (expression) of this viral anchor. Thus, the 'door' for the virus to enter lung cells becomes closed. This natural approach has the potential to control the current pandemic.

This study shows that vitamin C used individually and in combination with select natural bioactive compounds can inhibit expression of ACE2 receptor protein, which has attracted wide scientific interests as the primary cellular entry route for SARS-CoV-2 causing the current COVID-19 pandemic. We observed that ascorbic acid by itself can decrease cellular expression of ACE2 receptors in lung small airway epithelial cells (SAEC) and human microvascular endothelial cells (HMEC) at the protein and the RNA levels.

The inhibitory effect of ascorbic acid on ACE2 expression was seen at its higher concentrations (between 0.8 and 1 mM) and after 6 days of cell exposure. This finding may be helpful in understanding some of the clinical aspects of the efficacy of ascorbic acid applied at high doses, for example, by intravenous application in COVID-19 patients. The intravenous delivery route enables achieving much higher than 1 mM plasma concentrations of ascorbic acid compared to its dietary intake and would among other possible mechanisms result in a decrease of ACE2 receptors.

Ascorbic acid concentration in blood plasma is rapidly declining after its intravenous infusion due to kidney clearance. However, they allow sustainable intracellular ascorbic acid accumulation up to 10 mM level. 11 Similar effects occur in cell culture medium. Ascorbic acid content in medium in cell culture medium is rapidly declining within hours after cell supplementation due to ascorbic acid oxidation. However, even with fresh cell culture medium supplementations every 2 or 3 days there is a sustainable intracellular ascorbic acid accumulation. Therefore, the cell culture model could be regarded as a valid representation of the corresponding in vivo conditions. Interpretation of the results could be less straightforward with lung epithelial cells as the changes in ascorbic content in alveolar epithelium after its intravenous injections have not been yet characterized. Investigation of molecular mechanisms of ascorbic acid effects and its physiological implications for RAAS and viral infectivity was beyond the scope of this study and it should be a focus of further investigations. However, in our assumption the observed cellular effects of ascorbic acid on ACE2 protein expression were due rather its intracellular than extracellular action. Our experimental results indicate that longer exposure to ascorbic acid would be needed to obtain measurable inhibitory effects. Ascorbyl palmitate was more effective than ascorbic acid in lowering ACE2 and at much lower concentrations since this lipid-soluble compound can easily cross cellular membranes and is more stable than ascorbic acid.

Another novel aspect of our study includes experimental proof of the efficacy of various natural compounds in inhibiting expression of ACE2 receptors, which can be further enhanced by their interactions with ascorbic acid. While some molecular modeling studies indicated the potential of individual natural compounds against coronavirus, 13 they did neither include experimental testing nor evaluate the eventual synergistic effects of their combinations. Experimental evidence of the efficacy of natural compounds in addressing specific mechanisms associated with coronavirus infection is scarce, and to our knowledge does not address ACE2 expression. All compounds selected in our study demonstrated cooperative effects with ascorbic acid, albeit to various degrees. Several review studies suggested a possible therapeutic use of vitamin C and other natural compounds in COVID-19 patients as an adjunct to pharmacological treatments. Except of vitamin C which has been used clinically in COVID-19 patients, these recommendations are generally based on reviewing available data on general anti-viral and immune enhancing effects of natural compounds.

The present study, however, is the first systematic experimental approach to evaluate natural compounds that work in synergy with ascorbate to impede key mechanisms of coronavirus infection. Baicalein and theaflavine used individually and in combination with ascorbic acid could be beneficial in coping with the COVID-19 pandemic, by among other significantly decreasing cellular ACE2 receptors expression in SAEC. Theaflavin combined with ascorbate showed the strongest 87% inhibition of ACE2 expression. Our findings show that vitamin C has a consistent and significant lowering effect on ACE2 expression exercised at different molecular levels in human alveolar epithelial cells, but also in microvascular endothelial cells—the 2 main cell types affected by the SARS-CoV-2. In microvascular endothelial cells, ascorbic acid could inhibit ACE2 expression at the protein (Western blot) and RNA levels. The results of our study indicate that ascorbic acid—dependent modulation of the expression of ACE2 receptor in SAEC and HVEC cells could be at least 1 of the cellular mechanisms involved in producing beneficial therapeutical effects of intravenous ascorbate supplementation in critically ill patients with COVID-19. Furthermore, the results suggest that combinations of ascorbic acid with select natural compounds could further enhance its efficacy which should be taken into consideration in the future efforts to research and design preventive and therapeutic health approaches to the current pandemic.

What is claimed is:

1. A pharmaceutical composition to reducing or inhibiting the expression of an angiotensin converting enzyme 2 (ACE2) receptors in a mammal, comprising:

an ascorbic acid in the range of 10 mg to 200000 mg;

a baicalein as an additional compound present up to 2,000 mg;

a theaflavin as an additional compound amount is present up to 2,000 mg;

a zinc aspartate amount is in the range of 0.1 mg-200 mg (as elemental zinc);

a licorice in the range of 1 mg-200 mg/day; and a 10-undecenoic acid in the range of 1 mg-200 g.

2. A pharmaceutical composition of claim 1, wherein the ascorbic acid is one selected from L-ascorbic acid, magnesium ascorbate, calcium ascorbate, ascorbyl palmitate, ascorbyl phosphate, sodium ascorbyl phosphate and ascorbate and a combination thereof.

3. The pharmaceutical composition according to claim 2 is effective in a treatment of an infectious diseases related to viral entry using ACE2 receptor.

4. The pharmaceutical composition according to claim 2 is effective in a treatment of viral infections and/or viral diseases in a human and other species.

5. The pharmaceutical composition according to claim 4 is effective in a treatment of the viral infections that use a cellular receptor for a viral entry on a surface of a cell type that contains an ACE2 receptor.

6. The pharmaceutical composition according to claim 1 is effective in the treatment of the viral infections and/or diseases that use an angiotensin converting enzyme 2 (ACE2) receptor on the surface of a cell type that contains an ACE2 receptor.

7. The pharmaceutical composition according to claim 2 is effective in treatment of infections with Severe acute respiratory syndrome-related coronaviruses (SARS-CoV-1) that uses angiotensin converting enzyme 2 (ACE2) receptors on the surface of epithelial cells, endothelial cells and a cell type that contains an ACE2 receptor.

8. The pharmaceutical composition according to claim 2 is effective in treatment of infections with a Middle East respiratory syndrome-related coronavirus (MERS-CoV) that uses the angiotensin converting enzyme 2 (ACE2) receptor on the surface of epithelial cells, endothelial cells and a cell type that contains an ACE2 receptor.

9. The pharmaceutical composition of claim 2, wherein the L-ascorbic acid amount is in the range of 10 mg to 200000 mg for mammal consumption.

10. A pharmaceutical composition, consisting of:

An ascorbic acid amount is in the range of 10 mg to 200000 mg;

A baicalein and a theaflavin amount are individually present up to 2,000 mg;

A zinc aspartate amount is in the range of 0.1 mg-200 mg (as elemental zinc);

A licorice in the range of 1 mg-200 mg/day; and

A 10-undecenoic acid in the range of 1 mg-200 g for a mammal consumption.

* * * * *

SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: ACE2 FORWARD PRIMER

<400> SEQUENCE: 1
tgggcaaact ctatgctg                                                 18

<210> SEQ ID NO 2
<211> LENGTH: 20
<212> TYPE: DNA
<213> ORGANISM: Artificial Sequence
<220> FEATURE:
<223> OTHER INFORMATION: ACE2 REVERSE PRIMER

<400> SEQUENCE: 2

-continued

```
ttcattggct ccgtttctta                                                 20

<210> SEQ ID NO 3
<211> LENGTH: 25
<212> TYPE: DNA
<213> ORGANISM: Artificial Sequence
<220> FEATURE:
<223> OTHER INFORMATION: BETA ACTIN FORWARD PRIMER

<400> SEQUENCE: 3
catccgtaaa gacctctatg ccaac                                           25

<210> SEQ ID NO 4
<211> LENGTH: 19
<212> TYPE: DNA
<213> ORGANISM: Artificial Sequence
<220> FEATURE:
<223> OTHER INFORMATION: BETA ACTIN REVERSE PRIMER

<400> SEQUENCE: 4
atggagccac cgatccaca                                                  19
```